(12) United States Patent
Elliott

(10) Patent No.: US 6,214,846 B1
(45) Date of Patent: Apr. 10, 2001

(54) SUBSTITUTED 3-(BENZYLAMINO) PIPERIDINE DERIVATIVES AND THEIR USE AS THERAPEUTIC AGENTS

(75) Inventor: Jason Matthew Elliott, Felsted (GB)

(73) Assignee: Merck Sharp & Dohme Limited, Hoddesdon ( * ) Notice: Subject to any disclaimer, the term of this patent is extended or adjusted under 35 U.S.C. 154(b) by 0 days.

(21) Appl. No.: 09/445,664

(22) PCT Filed: Jun. 23, 1998

(86) PCT No.: PCT/GB98/01856

§ 371 Date: Dec. 9, 1999

§ 102(e) Date: Dec. 9, 1999

(87) PCT Pub. No.: WO99/00368

PCT Pub. Date: Jan. 7, 1999

(30) Foreign Application Priority Data

Jun. 27, 1997 (GB) .................................................. 9713715
Oct. 3, 1997 (GB) .................................................. 9720998

(51) Int. Cl.⁷ ........................ C07D 211/56; A61K 31/445
(52) U.S. Cl. .......................... 514/331; 514/314; 514/329; 546/223
(58) Field of Search ................................. 514/314, 329, 514/331; 546/223

(56) References Cited

U.S. PATENT DOCUMENTS 5,721,255 * 2/1998 Howaard et al. ..................... 514/329
5,925,627 * 7/1999 Baker et al. ............................ 514/90

FOREIGN PATENT DOCUMENTS

| 627221 | * 7/1994 | (EP) . |
| 0 780 375 A1 | 6/1997 | (EP) . |
| WO 91/18878 | 12/1991 | (WO) . |
| WO 93/11110 | 6/1993 | (WO) . |
| WO 95/08549 | 3/1995 | (WO) . |

* cited by examiner

*Primary Examiner*—Ceila Chang
(74) *Attorney, Agent, or Firm*—J. Eric Thies; David L. Rose

(57) ABSTRACT

The present invention relates to compounds of formula (I), wherein $R^1$ represents a fluoro$C_{1-2}$alkoxy group; and $R^2$ represents a hydrogen or halogen atom or a $C_{1-4}$alkyl, $C_{1-4}$alkoxy, fluoro$C_{1-4}$alkyl or fluoro$C_{1-4}$alkoxy group; or a pharmaceutically acceptable salt thereof. The compounds are of particular use in the treatment or prevention of pain or inflammation, migraine, emesis, postherpetic neuralgia, depression or anxiety.

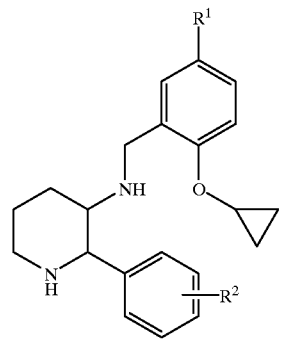

(I)

9 Claims, No Drawings

SUBSTITUTED 3-(BENZYLAMINO) PIPERIDINE DERIVATIVES AND THEIR USE AS THERAPEUTIC AGENTS

This application is a 371 of PCT/GB98/01856 filed Jun. 23, 1998.

This invention relates to piperidine derivatives and their use as tachykinin antagonists, and in particular as neurokinin-1 receptor antagonists.

We have now found a class of piperidine derivatives which are potent receptor antagonists of tachykinins, especially of the neurokinin-1 (substance P) receptor. In addition, the compounds of the present invention exhibit a high level of hepatic stability as measured by, for example, conventional liver microsome analysis.

Furthermore, by virtue of their unique cyclopropyl ether moiety, the compounds of the present invention possess a high degree of oral bioavailability together with high affinity for the human $NK_1$ receptor.

$NK_1$ antagonist piperidine derivatives are disclosed in International Patent Publicatioin No. WO-A-9300331.

The present invention provides the compounds of the formula (I):

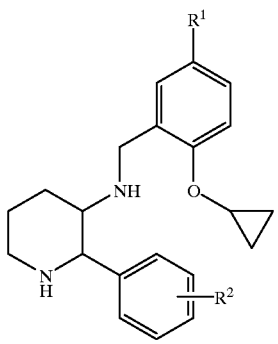

(I)

wherein $R^1$ represents a fluoro$C_{1-2}$alkoxy group; and $R^2$ represents a hydrogen or halogen atom or a $C_{1-4}$alkyl, $C_{1-4}$alkoxy, fluoro$C_{1-4}$alkyl or fluoro$C_{1-4}$alkoxy group;

or a pharmaceutically acceptable salt thereof.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-4}$alkyl" and "fluoro$C_{1-4}$alkoxy" means a $C_{1-4}$alkyl or $C_{1-4}$alkoxy group in which one or more (in particular, 1 to 3) hydrogen atoms have been replaced by fluorine atoms. Similarly, the term "fluoro$C_{1-2}$alkoxy" means a methoxy or ethoxy group in which one or more (in particular 1 to 3) hydrogen atoms have been replaced by fluorine atoms. Particularly preferred are fluoro$C_{1-2}$alkyl and fluoro$C_{1-2}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$, $OCHF_2$ and $OCH_2CF_3$.

Particularly preferred compounds of formula (I) are those wherein $R^1$ represents $OCF_3$, $OCHF_2$, $OCH_2F$ or $OCH_2CF_3$. Most especially, $R^1$ represents $OCF_3$.

Further preferred compounds of formula (I) are those wherein $R^2$ represents a hydrogen, fluorine or chlorine atom or a methyl, methoxy or trifluoromethoxy group. Especially preferred are those compounds of formula (I) wherein $R^2$ is a hydrogen atom, a 4-fluorine atom or a 3-trifluoromethoxy group. Most especially, $R^2$ is a hydrogen atom or a 4-fluorine atom.

A particularly preferred compound of the present invention is the compound of formula (Ia)

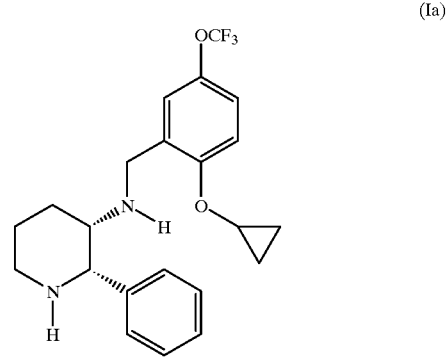

(Ia)

or a salt thereof, especially a pharmaceutically acceptable acid addition salt thereof. Most aptly the compounds of the formula (I) and (Ia) are the (2S,3S) stereoisomer.

Specific compounds of the present invention include:

N-{[2-cyclopropoxy-5-(trifluoromethoxy)phenyl]methyl}-2-phenylpiperidin-3-amine;

(2S,3S)-N-{[2-cyclopropoxy-5-(trifluoromethoxy)phenyl]methyl}-2-phenylpiperidin-3-amine;

N-{[2-cyclopropoxy-5-(trifluoromethoxy)phenyl]methyl}-2-(4-fluorophenyl)piperidin-3-amine;

or a pharmaceutically acceptable salt thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula (I) and salts thereof, for example, hydrates.

The compounds according to the invention have at least two asymmetric centres, and may accordingly exist both as enantiomers and as diastereoisomers. It is to be understood that all such isomers and mixtures thereof are encompassed within the scope of the present invention. The 2S,3S stereoisomer is particularly preferred.

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, bronchospasm and cough; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide or domperidone or GABAB receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or depression.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I)

and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal, especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The compounds of the present invention are also of use in the treatment or prevention of mania, including hypomania.

The present invention accordingly provides the use of a compound of formula (I) for the manufacture of a medicament for the treatment or prevention of mania, including hypomania.

The present invention also provides a method for the treatment or prevention of mania, including hypomania, which method comprises administration to a patient in need of such treatment of an effective amount of a compound of formula (I).

In a further aspect of the present invention, there is provided a pharmaceutical composition for the treatment or prevention of mania, including hypomania, comprising a compound of formula (I), together with at least one pharmaceutically acceptable carrier or excipient.

It will be appreciated that a combination of a conventional antipsychotic drug with a compound of formula (I) may provide an enhanced effect in the treatment of mania, including hypomania.

Thus, according to a further aspect of the present invention there is provided the use of a compound of formula (I) and an antipsychotic agent for the manufacture of a medicament for the treatment or prevention of mania, including hypomania.

The present invention also provides a method for the treatment or prevention of mania, including hypomania, which method comprises administration to a patient in need of such treatment of an amount of a compound of formula (I) and an amount of an antipsychotic agent, such that together they give effective relief.

In a further aspect of the present invention, there is provided a pharmaceutical composition comprising a compound of formula (I) and an antipsychotic agent, together with at least one pharmaceutically acceptable carrier or excipient.

It will be appreciated that the compound of formula (I) and the antipsychotic agent may be present as a combined preparation for simultaneous, separate or sequential use for the treatment or prevention of mania, including hypomania. Such combined preparations may be, for example, in the form of a twin pack.

In a further or alternative aspect of the present invention, there is therefore provided a product comprising a compound of formula (I) and an antipsychotic agent as a combined preparation for simultaneous, separate or sequential use in the treatment or prevention of mania, including hypomania.

The compounds of the present invention are also of use in the treatment or prevention of aggressive behaviour disorders.

The present invention accordingly provides the use of a compound of formula (1) for the manufacture of a medicament for the treatment or prevention of aggressive behaviour.

The present invention also provides a method for the treatment or prevention of aggressive behaviour, which method comprises administration to a patient in need of such treatment of an effective amount of a compound of formula (I).

In a further aspect of the present invention, there is provided a pharmaceutical composition for the treatment or prevention of aggressive behaviour comprising a compound of formula (I), together with at least one pharmaceutically acceptable carrier or excipient.

It will be appreciated that a combination of a conventional antipsychotic drug with a compound of formula (I) may provide an enhanced effect in the treatment of aggressive behaviour.

Thus, according to a further aspect of the present invention there is provided the use of a compound of formula (I) and an antipsychotic agent for the manufacture of a medicament for the treatment or prevention of aggressive behaviour.

The present invention also provides a method for the treatment or prevention of aggressive behaviour, which method comprises administration to a patient in need of such treatment of an amount of a compound of formula (I) and an amount of an antipsychotic agent, such that together they give effective relief.

It will be appreciated that the compound of formula (I) and the antipsychotic agent may be present as a combined preparation for simultaneous, separate or sequential use for the treatment or prevention of aggressive behaviour. Such combined preparations may be, for example, in the form of a twin pack.

In a further or alternative aspect of the present invention, there is therefore provided a product comprising a compound of formula (I) and an antipsychotic agent as a combined preparation for simultaneous, separate or sequential use in the treatment or prevention of aggressive behaviour.

As used herein, the term "aggressive behaviour" includes explosive personality disorder, intermittent explosive disorder, aggressive personality, aggressive nature, aggressiveness, excessive emotional instability, pathological emotionality, quarrelsomeness, dementia with behavioural disturbance, and personality change of the aggressive type due to a general medical condition.

Aggressive behaviour may also be associated with substance intoxication, substance withdrawal, oppositional defiant disorder, conduct disorder, antisocial personality disorder, borderline personality disorder, a manic episode and schizophrenia.

Suitable antipsychotic agents of use in combination with a compound of formula (I) include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a compound of formula (I) may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds according to the present invention may be prepared by a process (A) which comprises reacting a compound of formula (II) with a compound of formula (III) in the presence of a reducing agent:

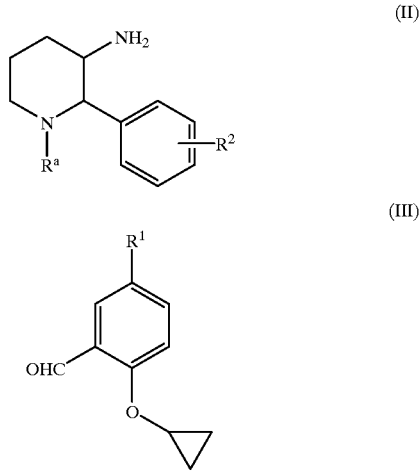

wherein $R^1$ and $R^2$ are as defined for formula (I), and $R^a$ is a hydrogen atom or a nitrogen protecting group.

Suitable reducing agents for use in this reaction include, for example, sodium borohydride, sodium cyanoborohydride or sodium triacetoxyborohydride. The reaction is conveniently effected in a suitable solvent such as acetic acid, methanol or 1,2-dichloroethane at a temperature between 0° C. and 50° C., conveniently at about room temperature.

According to another process (B), the compounds according to the present invention may be prepared by reacting a compound of formula (IV) with a compound of formula (V):

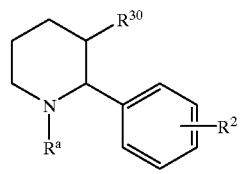

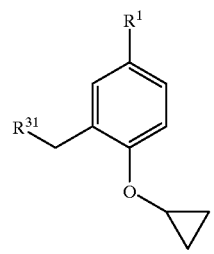

wherein $R^1$ and $R^2$ are as defined for formula (I), $R^a$ is a hydrogen atom or a nitrogen protecting group, and one of $R^{30}$ and $R^{31}$ represents a leaving group and the other of $R^{30}$ and $R^{31}$ represents $NH_2$; in the presence of a base, followed by deprotection, if required.

Suitably $R^{30}$ represents $NH_2$ and $R^{31}$ represents a leaving group.

Suitable leaving groups include halogen atoms, e.g. chlorine, bromine or iodine, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

According to another general process (C), compounds of formula (I) may be prepared from a compound of formula (VI)

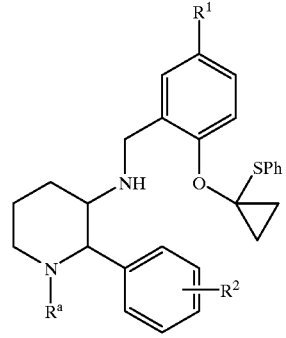

by reaction with lithium naphthalenide in tetrahydrofuran. The reaction is preferably effected at reduced temperature, for example at about −78° C.

Further details of suitable procedures will be found in the accompanying Examples.

Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl. Removal of the protecting group is effected by conventional procedures thus, for example, tert-butoxycarbonyl groups may be removed under acidic conditions using, for example, trifluoroacetic acid; benzyloxycarbonyl and benzyl groups, may also be removed by hydrogenolysis in the presence of a catalyst, for example, palladium; and trichloroethoxycarbonyl groups may be removed with zinc dust.

Methods for the preparation of intermediates of formula (II) and (IV) are well known in the art (see, for instance, European Patent Specification No. 0 436 334-A).

Intermediates of formula (III) may be prepared from a compound of formula (VII)

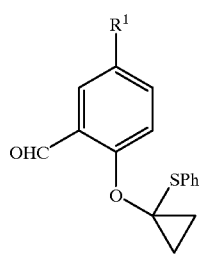

(VII)

using the method of general process (C), above.

Similarly, intermediates of formula (V) may be prepared from a compound of formula (VIII)

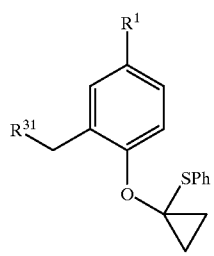

(VIII)

according to the method of general process (C).

Intermediates of formula (VI) may be prepared from a compound of formula (IX)

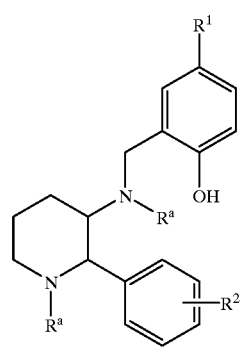

(IX)

wherein $R^1$ and $R^2$ are as defined for formula (I) and $R^a$ is a hydrogen atom or a nitrogen protecting group, by reaction with (1-iodo-cycloprop-1-yl)phenylsulphide in the presence of silver carbonate.

Compounds of formula (IX) may be prepared from a compound of formula (X)

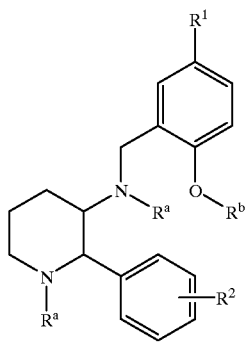

(X)

where $R^b$ is a suitable hydroxy protecting group, for example an aralkyl group such as benzyl, by hydrogenation under conventional conditions.

Compounds of formula (X) may be prepared by either of the methods of general process (A) or (B), above, using a suitable protected phenolic precursor of formula (XIa) or (XIb)

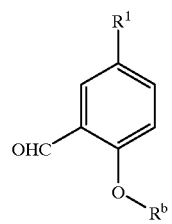

(XIa)

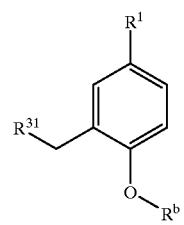

(XIb)

in place of the compound of formula (III) or (V), respectively.

Compounds of formulae (VII) and (VIII) may be prepared by reacting the corresponding phenolic precursors with (1-iodo-cycloprop-1-yl)phenylsulphide in the presence of silver carbonate. The phenolic precursors of compounds of formulae (VII), (VIII), (XIa) and (XIb) are known compounds or may be prepared from known compounds by methods readily apparent to one skilled in the art.

Alternatively, intermediates of formula (III) may be prepared by carbonylation of the corresponding aryl iodide using conventional methodology, for example, by treatment with carbon monoxide in the presence of tetrakis (triphenylphosphine)palladium (0) and tributyl tin hydride.

The aryl iodide precursor may be prepared from the corresponding aniline derivative using, for example, the methodology described herein.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The stereoisomers of the compounds of formula (I) may be separated by procedures known in the art to obtain the preferred (2S,3S) stereoisomers.

The exemplified compounds of this invention were tested by the methods set out at pages 36 to 39 of International Patent Specification No. WO 93/01165. The compounds were found to be active with $IC_{50}$ at the $NK_1$ receptor of less than 1 nM on said test method. Thus, for instance, the compounds of Examples 1 and 3 were found to have an $IC_{50}$ at the human $NK_1$ receptor of 0.17 nM and 0.2 nM, respectively.

The following non-limiting Examples serve to illustrate the preparation of compounds of the present invention:

Description 1

2-(1-Phenylthiocycloprop-1-yl)oxy-5-(trifluoromethoxy)benzaldehyde

Silver carbonate (1.2 g, 4.34 mmol) was added to a solution of 2-hydroxy-5-(trifluoromethoxy)benzaldehyde (0.5 g, 2.43 mmol) and (1-iodocycloprop-1-yl)phenylsulfide (Cohen T. and Matz J. R., *J. Am. Chem. Soc.* 1980, 102, 6902) (1.2 g, 4.34 mmol) in toluene (30 mL) and the mixture was stirred at 40° C. overnight. The mixture was cooled, diluted with ethyl acetate and filtered, washing well with ethyl acetate. The mixture was washed with aqueous sodium hydroxide, dried ($MgSO_4$) and the solvent was evaporated under reduced pressure. The residue was purified by flash column chromatography on silica gel, eluting with hexane/$Et_2O$ (95:5), to give the title compound as a yellow oil (191 mg, 27%). $^1$H NMR (360 MHz, $CDCl_3$) δ1.51–1.56 (2H, m), 1.44–1.48 (2H, m), 7.25–7.35 (7H, m), 7.69 (1H, d, J 2.0 Hz), and 10.26 (1H, s).

Description 2

2-Cyclopropoxy-5-(trifluoromethoxy)benzaldehyde

Freshly cut lithium metal (97 mg, 13.9 mmol) was added to a solution of naphthalene (1.77 g, 13.9 mmol) in THF (20 mL) and the mixture was sonicated at room temperature for 30 min. to produce a dark green solution of lithium naphthalenide. A solution of 2-(1-phenylthiocycloprop-1-yl)oxy-5-(trifluoromethoxy)benzaldehyde (Description 1, 96 mg, 0.27 mmol) in THF (2 mL) was cooled to −78° C. and the solution of lithium naphthalenide in THF (2 mL) was added dropwise until the intense green colour persisted. The reaction was then stirred for 5 min., water (6 mL) was added and the mixture was warmed to room temperature. The mixture was extracted with ethyl acetate, the combined organic fractions were dried ($MgSO_4$) and the solvent was evaporated under reduced pressure. The residue was purified by flash column chromatography on silica gel, eluting with hexane/$Et_2O$ (80:20), to give to give the title compound as a colourless oil (4 mg, 6%). $^1$H NMR (360 MHz, $CDCl_3$) δ0.86 (4H, m), 3.82–3.9 (1H, m), 7.42 (2H, m), 7.62 (1H, d, J 2.5 Hz), and 10.36 (1H, s).

Description 3

2-Nitro-4-(trifluoromethoxy)phenol

Iron(111)nitrate nonahydrate (1.97 g, 4.87 mmol) was added to a solution of 4-(trifluoromethoxy)phenol (2 g, 11.24 mmol) in ethanol (20 mL) and the mixture was heated under reflux overnight. The mixture was allowed to cool to room temperature, acidified to pH 1 with aqueous hydrochloric acid (1M) and extracted with ethyl acetate. The combined organic fractions were dried ($MgSO_4$), and the solvent was evaporated under reduced pressure. The residue was purified by short column chromatography on silica gel, eluting with hexane/EtOAc (70:30), to give the title compound as a yellow oil (2.25 g, 89%). $^1$H NMR (360 MHz, $CDCl_3$) δ10.53 (1H, s), 8.01 (1H, d, J 3.0 Hz), 7.49 (1H, dd, J 9.1, 3.0 Hz), and 7.23 (1H, d, J 9.1 Hz).

Description 4

2-(1-Phenylthiocycloprop-1-yl)oxy-5-(trifluoromethoxy)nitrobenzene

Prepared from the compound of Description 3 according to the method of Description 1. $^1$H NMR (360 MHz, $CDCl_3$) δ7.73 (1H, d, J 2.7 Hz), 7.58 (1H, d, J 9.2 Hz), 7.50–7.24 (6H, m), 1.57–1.53 (2H, m), and 1.44–1.40 (2H, m).

Description 5

2-Cyclopropoxy-5-(trifluoromethoxy)benzeneamine

Prepared from the compound of Description 4 according to the method of Description 2. $^1$H NMR (360 MHz, $CDCl_3$) δ7.06 (1H, dd, J 2.8, 6.7 Hz), 6.56 (2H, m), 3.83 (2H, br s), 3.74 (1H, m), and 0.79 (4H, m). m/z ($ES^+$) 234 (M+1).

Description 6

2-(1-Phenylthiocycloprop-1-yl)oxy-5-(trifluoromethoxy)benzeneamine

Iron powder (13.5 g, 241 mmol) was added to a suspension of 2-(1-phenylthiocycloprop-1-yl)oxy-5-(trifluoromethoxy)nitrobenzene (Description 4, 11.27 g, 30.1 mmol) in water (300 mL) and acetic acid (75 mL) and the mixture was stirred at 80° C. overnight. The mixture was cooled and filtered through celite, washing with ether. The filtrate was extracted with ether, the combined organic fractions were washed with aqueous sodium hydroxide (1M), dried ($MgSO_4$), and the solvent was evaporated under reduced pressure. The residue was purified by flash column chromatography on silica gel, eluting with hexane/$Et_2O$ (90:10 increasing to 80:20), to give the title compound as a yellow solid (8 g, 78%). $^1$H NMR (360 MHz, $CDCl_3$) δ7.48 (2H, m), 7.34–7.23 (3H, m), 7.15 (1H, d, J 8.74 Hz), 6.60–6.56 (2H, m), 3.78 (2H, br s), 1.49–1.46 (2H, m), and 1.39–1.35 (2H, m).

Description 7

2-Cyclopropoxy-5-(trifluoromethoxy)benzeneamine

Prepared from the compound of Description 6 according to the method of Description 2. $^1$H NMR (360 MHz, $CDCl_3$) δ7.06 (1H, dd, J 2.8, 6.7 Hz), 6.56 (2H, m), 3.83 (2H, br s), 3.74 (1H, m), and 0.79 (4H, m). m/z ($ES^+$) 234 (M+1).

Description 8

2-Cyclopropoxy-5-(trifluoromethoxy)iodobenzene

An ice-cooled solution of sodium nitrite (3.55 g, 51 mmol) in water (10 mL) was added dropwise to a stirred, cooled (0° C.) solution of 2-cyclopropoxy-5-(trifluoromethoxy)benzeneamine (Description 7, 4.8 g, 20.6 mmol) in aqueous hydrochloric acid (5M, 300 mL), maintaining the internal temperature at 0° C. The mixture was stirred at 0° C. for 30 min., then potassium iodide (8.55 g, 51.5 mmol) in water (10 mL) was added dropwise, maintaining the internal temperature at 0° C. The mixture was stirred at 0° C. for 30 min., then allowed to warm up to room temperature and stirred until nitrogen evolution ceased. The mixture was extracted with ether, the organic fraction was washed with aqueous sodium thiosulfate (10%), dried (MgSO4), and the solvent was evaporated under reduced pressure. The residue was purified by flash column chromatography on silica gel, eluting with hexane/Et$_2$O (98:2 increasing to 95:5), to give the title compound as a colourless oil (6.23 g, 88%). $^1$H NMR (360 MHz, CDCl$_3$) δ7.62 (1H, d, J 2.4 Hz), 7.20 (1H, dd, J 9.1, 2.4 Hz), 7.15 (1H, d, J 9.1 Hz), 3.80 (1H, m), and 0.83 (4H, m).

Description 9

2-Cyclopropoxy-5-(trifluoromethoxy)benzaldehyde

A solution of 2-cyclopropoxy-5-(trifluoromethoxy) iodobenzene (Description 8, 0.344 g, 1 mmol) in toluene (2.5 mL) was degassed with bubbling nitrogen for 10 min. Tetrakis(triphenylphosphine)palladium (0) (15 mg) was added, the mixture was degassed with bubbling nitrogen for a further 5 min., then carbon monoxide was bubbled through the mixture for 10 min. The mixture was warmed to 50° C. and a solution of tributyl tin hydride (0.3 mL, 1.1 mmol) in toluene (5 mL) was added at a rate of 2 mL/h. via a syringe pump, maintaining carbon monoxide bubbling throughout. The mixture was cooled, diluted with ether (20 mL) and aqueous potassium fluoride solution (50%) was added. The mixture was stirred at room temperature overnight, filtered and the layers were separated. The organic layer was dried (MgSO$_4$), and the solvent was evaporated under reduced pressure. The residue was purified by flash column chromatography on silica gel, eluting with hexane/Et$_2$O (80:20), to give the title compound as a colourless oil. $^1$H NMR (360 MHz, CDCl$_3$) δ0.86 (4H, m), 3.82–3.9 (1H, m), 7.42 (2H, m), 7.62 (1H, d, J 2.5 Hz), and 10.36 (1H, s).

Description 10

(±)-(2RS)-1-tert-Butoxycarbonyl-2-phenylpiperidin-3-one

Dimethyl sulfoxide (32.0 mL, 35.3 g, 0.45 mol) in dichloromethane (100 mL) was added dropwise to a cooled (−70° C.) solution of oxalyl chloride (18.7 mL, 27.5 g, 0.22 mol) in dichloromethane (1000 mL). The mixture was stirred at −70° C. for 15 min., then (2S,3S)-1-tert-butoxycarbonyl-3-hydroxy-2-phenylpiperidine (prepared by the method described in European Patent Specification number 0 528 495-A; 50 g, 0.18 mol) in dichloromethane (150 mL) was added dropwise. The mixture was stirred at −70° C. for 1 h., then triethylamine (125.8 mL, 91.3 g, 0.9 mol) was added slowly. The mixture was stirred at room temperature for 1 h., water (250 mL) and aqueous sodium hydrogen carbonate (saturated, 250 mL) were added and the mixture was stirred at room temperature overnight. The layers were separated and the aqueous layer was extracted with dichloromethane (2×300 mL). The combined organic fractions were washed with brine, dried (MgSO$_4$) and the solvent was evaporated under reduced pressure. The residue was purified by flash column chromatography on silica gel, eluting with hexane/EtOAc (90:10), to give the title compound as a yellow oil (45.0 g, 91%). $^1$H NMR (250 MHz, CDCl$_3$) δ7.5–7.3 (5H, m), 5.8 (1H, br s), 4.2 (1H, br s), 3.4 (1H, m), 2.6 m), 2.0 (2H, m), and 1.54 (9H, s).

Description 11

(±)-(2R3R,2S3S)-1-(tert-Butoxycarbonyl)-2-phenylpiperidin-3-amine

A solution of hydroxylamine hydrochloride (17 g, 0.24 mol) and sodium acetate (55.67 g, 0.41 mol) in water (150 mL) was added to a solution of (±)-(2RS)-1-tert-butoxycarbonyl-2-phenylpiperidin-3-one (Description 10, 45 g, 0.16 mol) in ethanol (300 mL) and the mixture was stirred at room temperature for 1 h. The solvent was evaporated under reduced pressure, water was added and the mixture was extracted with ethyl acetate. The organic fraction was washed with brine, dried (MgSO$_4$) and the solvent was evaporated under reduced pressure. The residue was dissolved in ethanol (400 mL) and Raney nickel (50 g) was added. The mixture was shaken under hydrogen (40 psi) overnight, filtered and the solvent was evaporated under reduced pressure. The residue was purified by flash column chromatography on silica gel, eluting with CH$_2$Cl$_2$/MeOH (100:0 increasing to 85:15), to give the title compound as a colorless oil (10.9 g, 24%). $^1$H NMR (360 MHz, CDCl$_3$) δ7.43 (2H, d, J 7.0 Hz), 7.30 (3H, m), 5.19 (1H, d, J 6.2 Hz), 4.00 (1H, m), 3.17 (2H, m), 1.90–1.64 (4H, m), 1.36 (9H, s), and 1.26 (2H, br s).

Description 12

2-(1-Phenylthiocycloprop-1-yl)oxy-5-(trifluoromethoxy)benzenemethanol

Silver carbonate (4.82 g, 17.5 mmol) was added to a solution of 2-hydroxy-5-(trifluoromethoxy)benzaldehyde (2.0 g, 9.7 mmol) and (1-iodocycloprop-1-yl)phenylsulfide (Cohen T. and Matz J. R., J. Am. Chem. Soc. 1980, 102, 6902) (5.48 g, 17.5 mmol) in toluene (25 mL) and the mixture was stirred at 40° C. for 36 h., then at room temperature for 16 h. The mixture was diluted with ethyl acetate and filtered, washing well with ethyl acetate. The mixture was washed with aqueous sodium hydroxide (1M, 6×75 mL) and brine (75 mL), dried (MgSO$_4$) and the solvent was evaporated under reduced pressure. The residue was dissolved in ethanol, (15 mL), cooled to 0° C. and sodium borohydride, (0.74 g, 19.6 mmol), was added. The mixture was stirred at room temperature for 1 h., poured into water and extracted into ethyl acetate (3×100 mL). The combined organic fractions were dried (MgSO$_4$), and the solvent was evaporated under reduced pressure. The residue was purified by flash column chromatography on silica gel, eluting with hexane/EtOAc (97:3 increasing to 70:30), to give the title compound as a yellow oil (1.8 g, 53%). $^1$H NMR (250 MHz, CDCl$_3$) 1.41–1.44 (2H, m), 1.46–1.51 (2H, m), 1.84 (1H, t, J 6.5 Hz), 4.58 (2H, d, J 6.5 Hz), and 7.18–7.48 (8H, m).

Description 13

2-Cyclopropoxy-5-(trifluoromethoxy)benzenemethanol

Prepared from the compound of Description 12 according to the method of Description 2. $^1$H NMR (360 MHz, CDCl$_3$) δ0.74–0.88 (4H, m), 2.14 (1H, t, J 6.5 Hz), 3.78 (1H, m), 4.62 (2H, d, J 6.5 Hz), and 7.10–7.26 (3H, m).

Description 14

2-Cyclopropoxy-5-(trifluoromethoxy)benzaldehyde

Sulfur trioxide pyridine complex (0.90 g, 5.7 mmol) was added to a solution of 2-cyclopropoxy-5-(trifluoromethoxy)

benzenemethanol (Description 13, 393 mg, 1.6 mmol) and triethylamine, (1.54 mL, 11.1 mmol) in dimethylsulfoxide (3 mL) and the mixture was stirred at room temperature for 45 min. Further triethylamine (0.44 mL, 3.2 mmol) and sulfur trioxide pyridine complex (0.126 g, 0.8 mmol) were added and the mixture was stirred at room temperature for 30 min. The mixture was poured into aqueous citric acid (10%, 50 mL) and extracted with ethyl acetate. The combined organic fractions were washed with aqueous citric acid (10%, 3×50 mL) and water (3×50 mL), dried ($Na_2SO_4$), and the solvent was evaporated under reduced pressure to give the title compound as an orange oil (0.326 g, 84%). $^1$H NMR (360 MHz, $CDCl_3$) δ0.86 (4H, m), 3.82–3.9 (1H, m), 7.42 (2H, m), 7.62 (1H, d, J 2.5 Hz), and 10.36 (1H, s).

EXAMPLE 1

(±)-(2R3R,2S3S)-N-{[2-Cyclopropoxy-5-(trifluoromethoxy)phenyl]methyl}-2-phenylpiperidin-3-amine Dihydrochloride 2-Cyclopropoxy-5-(trifluoromethoxy)benzaldehyde (Description 9, 55 mg, 0.21 mmol) was added to (±)-(2R3R, 2S3S)-1-(tert-butoxycarbonyl)-2-phenylpiperidin-3-amine (Description 11, 58 mg, 0.21 mmol), citric acid (89 mg, 0.42 mmol) and 3 Å molecular sieves in dry methanol (5 mL) and the mixture was stirred at room temperature for 1.5 h. Sodium borohydride (30 mg) was added and the mixture was stirred at room temperature for 2 h. Ethyl acetate was added and the mixture was washed with aqueous hydrochloric acid (0.1M, 2×25 mL) and brine (25 mL), dried ($MgSO_4$) and the solvent was evaporated under reduced pressure. The residue was dissolved in dichloromethane (3 mL), cooled to 0° C. and trifluoroacetic acid (2 mL) was added slowly. The mixture was stirred at room temperature for 1 h., the solvent was evaporated under reduced pressure and ethyl acetate was added. The mixture was washed with aqueous sodium hydrogen carbonate (saturated, 2×25 mL) and brine (25 mL), dried ($MgSO_4$) and the solvent was evaporated under reduced pressure. The residue was purified by flash column chromatography on silica gel, eluting with $CH_2Cl_2$/MeOH/$NH_3$(Aq.) (96:4:0.4). The residue was dissolved in ethanol (2 mL), cooled in ice and ethereal hydrogen chloride (1M, 0.24 mL, 0.24 mmol) was added. The solvent was evaporated under reduced pressure and the residue was recrystallised from ethanol to give the title compound as a colorless solid (20 mg, 20%). m.p. 169–171° C. $^1$H NMR (400 MHz, $CD_3OD$) δ0.64 (1H, m), 0.80 (3H, m), 1.99 (1H, m), 2.24 (1H, m), 2.46 (2H, m), 3.30 (1H, m), 3.64 (1H, m), 3.75 (2H, m), 3.96 (1H, br s), 4.08 (1H, m), 4.95 (1H, s), 7.23 (1H, s), 7.31 (1H, d, J 9.0 Hz), 7.37 (1H, d, J 9.0 Hz), 7.54 (3H, m), and 7.67 (2H, m). m/z ($ES^+$) 407 (M+1).

EXAMPLE 2

(2S3S)-N-{[2-Cyclopropoxy-5-(trifluoromethoxy)phenyl]methyl}-2-phenylpiperidin-3-amine Dihydrochloride Sodium triacetoxyborohydride (411 mg, 1.94 mmol) was added to a mixture of 2-cyclopropoxy-5-(trifluoromethoxy) benzaldehyde (Description 9, 159 mg, 0.646 mmol), (2S3S)-2-phenylpiperidin-3-amine (prepared by the method described in WO 95/08549, 171 mg, 0.97 mmol) and acetic acid, (111 μl, 1.94 mmol) in 1,2-dichloroethane (5 mL) and the mixture was stirred at room temperature for 2.5 h. The mixture was poured into aqueous sodium hydrogen carbonate (satd., 50 mL) and extracted with ethyl acetate. The combined organic fractions were washed with aqueous sodium hydrogen carbonate (satd., 2×50 mL) and brine (50 mL), dried ($Na_2SO_4$) and the solvent was evaporated under reduced pressure. The residue was purified by MPLC on silica gel, eluting with $CH_2Cl_2$/MeOH/$NH_3$(Aq.) (97:3:0.3). The residue was dissolved in ethanol (2 mL) and ethanolic hydrogen chloride (5M, 0.5 mL) was added. The solid was collected and recrystallised from ethanol. The solid was collected and dried in vacuo to give the title compound as a yellow solid (144 mg, 46%). m.p. 168–171° C. $^1$H NMR (360 MHz, $CD_3OD$) δ0.66–0.67 (1H, m), 0.80–0.82 (3H, m), 1.99–2.03 (1H, m), 2.27–2.35 (1H, m), 2.43–2.54 (2H, m), 3.30 (1H, m), 3.57–3.68 (1H, m), 3.75–3.80 (2H, m), 4.06–4.14 (2H, m), 5.05–5.06 (1H, d, J 2.7 Hz), 7.26 (1H, d, J 2.0 Hz), 7.30–7.39 (2H, m), 7.50–7.57 (3H, m), and 7.61 (2H, m). m/z ($ES^+$) 407 (M+1).

EXAMPLE 3

(±)-(2R3R,2S3S)-N-{[2-Cyclopropoxy-5-(trifluoromethoxy)phenyl]methyl}-2-(4-fluorophenyl)piperidin-3-amine Dihydrochloride Prepared from the compound of Description 9 and (±)-(2R3R,2S3S)-2-(4-fluorophenyl)piperidin-3-amine (prepared by the method described in WO 95/08549) according to the method of Example 2. m.p. 187–189° C. $^1$H NMR (360 MHz, $CD_3OD$) δ0.62–0.68 (1H, m), 0.73–0.83 (3H, m), 1.94–1.99 (1H, m), 2.16–2.20 (1H, m), 2.36–2.42 (2H, m), 3.24–3.34 (1H, m), 3.61–3.65 (1H, m), 3.77–3.85 (3H, m), 4.07–4.11 (1H, m), 4.68–4.93 (5H, m), 7.24–7.39 (5H, m), and 7.67–7.70 (2H, m). m/z ($ES^+$) 425 (M+1). Found: C, 52.75; H, 5.14; N, 5.43. $C_{22}H_{24}F_4N_2O_2$.2HCl requires: C, 53.13; H, 5.27; N, 5.63%.

The following examples illustrate pharmaceutical compositions according to the invention.

EXAMPLE 4

| Tablets containing 50–300 mg of a compound of formula (I) | | | |
|---|---|---|---|
| | Amount mg | | |
| Compound of formula (I) | 50.0 | 100.0 | 300.0 |
| Microcrystalline cellulose | 80.0 | 80.0 | 80.0 |
| Modified food corn starch | 80.0 | 80.0 | 80.0 |
| Lactose | 189.5 | 139.5 | 139.5 |
| Magnesium Stearate | 0.5 | 0.5 | 0.5 |

The active ingredient, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the NK-1 receptor antagonist per tablet.

EXAMPLE 5

| Parenteral injection | |
|---|---|
| | Amount |
| Active Ingredient | 10 to 300 mg |
| Citric Acid Monohydrate | 0.75 mg |
| Sodium Phosphate | 4.5 mg |

| Parenteral injection | |
|---|---|
| | Amount |
| Sodium Chloride | 9 mg |
| Water for injection | to 10 ml |

The sodium phosphate, citric acid monohydrate and sodium chloride are dissolved in a portion of the water. The active ingredient is dissolved or suspended in the solution and made up to volume.

What is claimed is:

1. A compound of the formula (I):

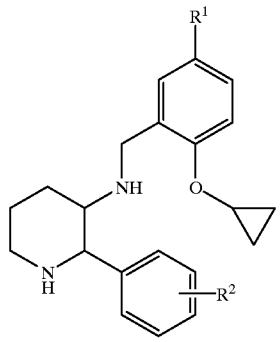

(I)

wherein

R$^1$ represents a fluoroC$_{1-2}$alkoxy group; and

R$^2$ represents a hydrogen or halogen atom or a C$_{1-4}$alkyl, C$_{1-4}$alkoxy, fluoroC$_{1-4}$alkyl or fluoroC$_{1-4}$alkoxy group;

or a pharmaceutically acceptable salt thereof.

2. A compound as claimed in claim 1 wherein R$^1$ represents OCF$_3$, OCHF$_2$, OCH$_2$F or OCH$_2$CF$_3$.

3. A compound as claimed in claim 1 wherein R$^2$ represents a hydrogen, fluorine or chlorine atom or a methyl, methoxy or trifluoromethoxy group.

4. A compound as claimed in claim 1 of formula (Ia)

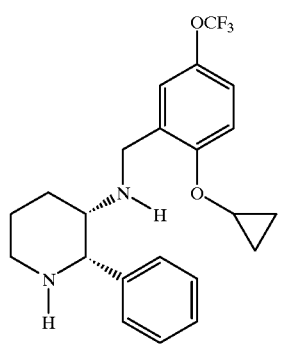

(Ia)

or a salt thereof.

5. The compound as claimed in claim 4 in the form of a pharmaceutically acceptable acid addition salt.

6. A compound as claimed in claim 1 in the form of its (2S,3S) stereoisomer.

7. A compound which is selected from:

N-{[2-cyclopropoxy-5-(trifluoromethoxy)phenyl]methyl}-2-phenylpiperidin-3-amine;

(2S,3S)-N-{[2-cyclopropoxy-5-(trifluoromethoxy)phenyl]methyl}-2-phenylpiperidin-3-amine;

N-{[2-cyclopropoxy-5-(trifluoromethoxy)phenyl]methyl}-2-(4-fluorophenyl)piperidin-3-amine;

or a pharmaceutically acceptable salt thereof.

8. A pharmaceutical composition comprising a therepeutically effective amount of a compound as claimed in claim 1, together with at least one pharmaceutically acceptable carrier or excipient.

9. A process for the preparation of a compound as claimed in claim 1 which comprises:

(A) reacting a compound of formula (II) with a compound of formula (III) in the presence of a reducing agent:

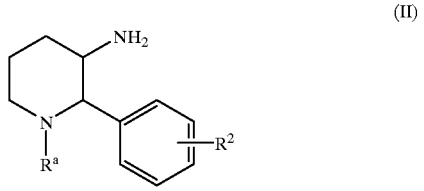

(II)

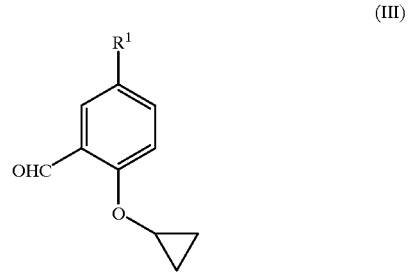

(III)

wherein R$^1$ and R$^2$ are as defined in claim 1, and R$^a$ is a hydrogen atom or a nitrogen protecting group; or (B) reacting a compound of formula (IV) with a compound of formula (V):

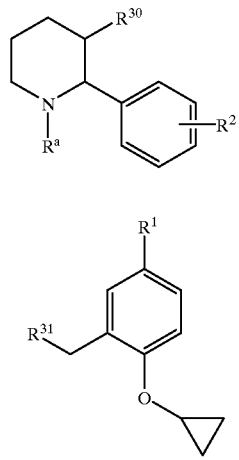

wherein $R^1$ and $R^2$ are as defined in claim 1, $R^a$ is a hydrogen atom or a nitrogen protecting group, and one of $R^{30}$ and $R^{31}$ represents a leaving group and the other of $R^{30}$ and $R^{31}$ represents $NH_2$; in the presence of a base; or (C) reacting a compound of formula (VI)

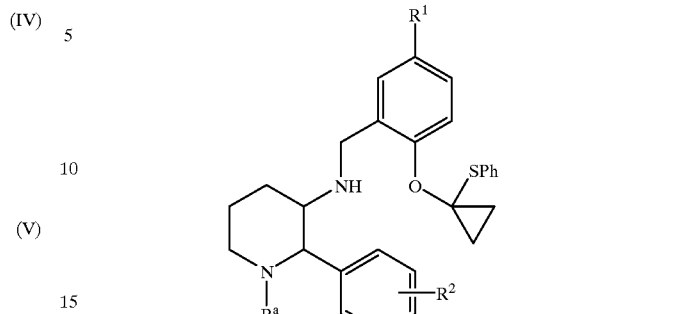

with lithium naphthalenide in tetrahydrofuran;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *